United States Patent [19]

Brimm et al.

[11] Patent Number: 5,072,383
[45] Date of Patent: * Dec. 10, 1991

[54] MEDICAL INFORMATION SYSTEM WITH AUTOMATIC UPDATING OF TASK LIST IN RESPONSE TO ENTERING ORDERS AND CHARTING INTERVENTIONS ON ASSOCIATED FORMS

[75] Inventors: John E. Brimm, Scottsdale; Oscar R. Diaz; Murray A. Fein, both of Phoenix; Ronald E. Norden-Paul, Peoria, all of Ariz.; Michael M. Stern, Needham, Mass.; Sandra L. Stewart, Phoenix, Ariz.

[73] Assignee: Emtek Health Care Systems, Inc., Tempe, Ariz.

[*] Notice: The portion of the term of this patent subsequent to Jun. 5, 2007 has been disclaimed.

[21] Appl. No.: 572,315

[22] Filed: Aug. 24, 1990

Related U.S. Application Data

[63] Continuation of Ser. No. 268,323, Nov. 19, 1988, abandoned.

[51] Int. Cl.$^5$ .............................................. G06F 15/42
[52] U.S. Cl. ........................ 364/413.02; 364/413.02; 340/121
[58] Field of Search ................... 364/401, 408, 413.02, 364/413.01, 922, 224.5; 340/721, 717

[56] References Cited

U.S. PATENT DOCUMENTS 4,489,387 12/1984 Lamb et al. ..................... 364/413.02

OTHER PUBLICATIONS

"An Integrated Bedside Fetal Monitor and Obstetrical Data System", IEEE Eng. In. Med. & Biology Med., Sep. 1984, pp. 22-24.
"U.S. Healthcare", vol. 6, No. 3, Mar. 1989.
J. E. Brimm, Computers in Critical Care, Mar. 1987, pp. 53-63, Critical Care Nursing Quarterly.
Hewlett Packard, 78707A PDMS Clinical User's Guide, Jan. 1982, pp. i-1 thru 1-34, 10-1 thru 10-5, 15-1 thru 15-2.
Hewlett Packard, PDMS System Description, 1982, pp. 1-1 thru 2-23.
Health Data Sciences Corp., Ulticare (presumably 10/84), pp. 1-9.
Ralph A. Korpman, "Patient Care Information Systems-Looking to the Future", Software in Healthcare, Parts 1-5, Apr./May 1984-Dec./Jan. 1984-85.

Primary Examiner—Gail O. Hayes
Attorney, Agent, or Firm—Walter W. Nielsen

[57] ABSTRACT

A hospital information system comprises a data processing system including a plurality of terminals having display means and data entry means. Patient information is entered into the system via the terminals, is organized hierarchically in the system, and may be displayed to users having proper access to the system. The system provides a time-oriented task list, which is automatically generated from data which has been entered from physicians' and nursing orders. Tasks may be charted by a system user directly onto a system form, and the task list and any associated form(s) are automatically updated.

2 Claims, 12 Drawing Sheets

FIG. 4

| METRO MEDICAL CENTER | | | | | JAN 07 06:00 | |
|---|---|---|---|---|---|---|
| CENSUS: | 2NTU | 9NBURN | MICU | 9NICU | CCU | INACTIVE PTS |
| ROOM/BED | PATIENT NAME | | | PATIENT ID | | ADMIT DATE |
| 201 | THURMAN, AUDREE L. | | | 87-3-77 | | 12-01-87 |
| 202 | [EMPTY BED] | | | | | |
| 203 | OSTLER, MICHAEL L. | | | 87-3-85 | | 11-25-87 |
| 204 | JACKSON, DONALD M. | | | 87-19-46 | | 01-03-88 |
| 205 | | | | | | |
| 206 | | | | | | |
| 207 | | | | | | |
| 208 | | | | | | |

72   74   76   78

82   84 TRANSFER   86 DISCHARGE   88 OPEN CHART   89

FIG. 5

METRO MEDICAL CENTER     JAN 05 09:00

150  JACKSON, DONALD M.   60  M  9NBURN
ATTENDING: CHARLES RICE, M.D.    MR#: 88-19-46

SECTIONS: FLOWSHEET [ORDERS] NCP ASSESSMENT LABS R.T. KARDEX — 203

FORMS: [ORDER SHEET] ORDER HISTORY — 209

| | ORDER TEXT | STATUS | ORDER DATE / TIME | MD | CR / LN |
|---|---|---|---|---|---|
| MEDS | DIGOXIN 0.125 mg IV qd | ACTIVE | 01/05 0900 | | / LN |
| | MORPHINE SULFATE 1-5 mg IV q4h PRN SEVERE PAIN | | | | / LN |
| | AMPICILLIN 500 m | | | | / LN |
| IV'S | 500cc HS FLUSH S 1000 UNITS HEPARI | | | | / LN |
| | 250cc D5W LEFT A 50 mg NIPRIDE | | | | / LN |
| | 500cc D5W TKO LE | | | | / LN |
| LAB | H & H | | | | / LN |
| | LYTES | | | | / LN |
| | EKG | | | | / LN |
| | HCL1 | | | | / LN |

MEDICATION ORDER ENTRY

ORDER DATE: 01/05
ORDER TIME: 0900
ORDERING MD: CR — 200
DRUG NAME: ____ — 269
ROUTE:
DOSE:
FREQUENCY:
NUMBER OF DOSES:
START DATE: 01/05/88
START TIME: 0900
STOP DATE: 01/08/88
STOP TIME: 0900
COMMENTS:

— 263

SELECT— ↑ [PREV PAGE] ↑
16) INSULIN, LENTE
17) INSULIN, REGULAR
18) LEVOPHED
19) LIDOCAINE
20) MORPHINE SULFATE
21) NIPRIDE
22) PERCOCET
23) PERSANTINE
24) PHENOBARBITAL INJECTION
25) PHENOBARBITAL TABLET
26) RITODRINE
27) TYLENOL ELIXIR
28) TYLENOL TABLET
29) VALIUM INJECTION
30) VALIUM TABLET
→ [NEXT PAGE] →

METRO MEDICAL CENTER  JAN 07 0912

BLOOD GAS RESULTS READY

JACKSON, DONALD M.  9NBURN
ATTENDING: CHARLES RICE, M.D.  MR#: 88-19-46

SECTIONS: [FLOWSHEET] ORDERS  NCP  ASSESSMENT  LABS  R.T.  KARDEX

FORMS: [MAR] VITALS  I/O  VENTILATOR  LABS

| START STOP | MEDICATION DOSE ROUTE FREQUENCY | SCHED TIME | ACTUAL TIME | DOSE | ROUTE/SITE | COMMENTS | INITIAL |
|---|---|---|---|---|---|---|---|
| ROUTINE: | | | | | | | |
| 01/05 1200<br>02/01 0600 | AMPICILLIN  RIGHT ARM<br>500 mg IN 100cc D5W IVPB  q6h | 0600<br>1200<br>1800 | 0615 | 500mg | RIGHT ARM | | LN |
| 01/05 0600<br>01/07 1800 | MYLANTA II  NG  q4H | 0600<br>1000<br>1400<br>1800 | 0600 | 30cc | | | LN |
| DRIPS IV's: | | | | | | | |
| 01/05 0600 | NIPRIDE IN 250cc D5W LEFT ARM<br>10cc/HR. | | 0600 | 25mg | LEFT ARM | | LN |
| PRN: | | | | | | | |
| 01/05 0900<br>01/08 1900 | MORPHINE SULFATE<br>1.5mg   IV       q4H<br>PRN SEVERE PAIN | | 0700 | 5mg | IV | FOR PAIN WITH RELIEF | LN |
| 01/05 0900<br>01/08 0900 | VALIUM TABLET  2mg ORAL  q4H<br>PRN RESTLESSNESS | 0900 | 0911 | 2mg | ORAL | | [LN] |

SIGN

FIG. 7

| METRO MEDICAL CENTER | | JAN 07 0910 |
|---|---|---|
| BLOOD GAS RESULTS READY | JACKSON, DONALD M. | 9NBURN |
| | ATTENDING: CHARLES RICE, M.D. | MR#: 88-19-46 |

SECTIONS: FLOWSHEET ORDERS NCP ASSESSMENT LABS R.T. [KARDEX]

FORMS: [TASK LIST] DIAGNOSTIC STUDIES MEDICATIONS GENERAL CARE PERTINENT INFORMATION

| DATE | TIME | ORDER TEXT |
|---|---|---|
| 01/07 | 0800 | CHECK NIPRIDE INFUSION SITE |
| | 0800 | NEURO VITAL SIGNS |
| | 0800 | BAG & SUCTION USING STERILE TECHNIQUE |
| | 0800 | ASSESS LUNG SOUNDS |
| | 0900 | BED GROUNDED AND WHEELS LOCKED |
| | 0900 | CHECK NIPRIDE INFUSION SITE |
| | 0900 | COMPLETE BED BATH & SKIN CARE |
| | 0900 | VALIUM TABLET 2mg ORAL qd PRN RESTLESSNESS |
| | 0900 | CHECK NIPRIDE INFUSION SITE |
| | 1000 | FOLEY CATH CARE PER PROTOCOL |
| | 1000 | ET TUBE POSITION CHANGE |
| | 1200 | AMPICILLIN 500mg IVPB IN 100cc D5W q6H |
| | 1600 | MORPHINE SULFATE 1-5mg IV q4h PRN SEVERE PAIN |
| | 1800 | AMPICILLIN 500mg IVPB IN 100cc D5W q6H |
| | 2000 | MORPHINE SULFATE 1-5mg IV q4h PRN SEVERE PAIN |

[NEXT PAGE] [ADD]

FIG. 8A

METRO MEDICAL CENTER — JAN 07 0910

BLOOD GAS RESULTS READY

JACKSON, DONALD M.    9NBURN
ATTENDING: CHARLES RICE, M.D.    MR#: 88-19-46

SECTIONS: FLOWSHEET ORDERS NCP ASSESSMENT LABS R.T. KARDEX

FORMS: [TASK LIST] DIAGNOSTIC STUDIES MEDICATIONS GENERAL CARE PERTINENT INFORMATION

| DATE | TIME | ORDER TEXT |
|---|---|---|
| 01/07 | 0800 | CHECK NIPRIDE INFUSION SITE |
|  | 0800 | NEURO VITAL SIGNS |
|  | 0800 | BAG & SUCTION USING STERILE TECHNIQUE |
|  | 0800 | ASSESS LUNG SOUNDS |
|  | 0900 | BED GROUNDED AND WHEELS LOCKED |
|  | 0900 | CHECK NIPRIDE INFUSION SITE |
|  | 0900 | COMPLETE BED BATH & SKIN CARE |
|  | 0900 | [VALIUM TABLET 2mg ORAL qd PRN RESTLESSNESS] |
|  | 1000 | CHECK NIPRIDE INFUSION SITE |
|  | 1000 | FOLEY CATH CARE PER PROTOCOL |
|  | 1000 | ET TUBE POSITION CHANGE |
|  | 1200 | AMPICILLIN 500mg IVPB IN 100cc D5W q6H |
|  | 1600 | MORPHINE SULFATE 1-5mg IV q4h PRN SEVERE PAIN |
|  | 1800 | AMPICILLIN 500mg IVPB IN 100cc D5W q6H |
|  | 2000 | MORPHINE SULFATE 1-5mg IV q4h PRN SEVERE PAIN |

→ NEXT PAGE →

[CHART] [NON-TIME] [ADJUST]

FIG. 8B

| METRO MEDICAL CENTER | | | | JAN 07 0911 |
|---|---|---|---|---|
| BLOOD GAS RESULTS READY | | JACKSON, DONALD M. | | 9NBURN |
| | | ATTENDING: CHARLES RICE, M.D. | | MR#: 88-19-46 |

SECTIONS: FLOWSHEET ORDERS NCP ASSESSMENT LABS R.T.

FORMS: [TASK LIST] DIAGNOSTIC STUDIES MEDICATIONS GENERAL CARE PERTINENT INFORMATION [KARDEX]

| DATE | TIME | ORDER TEXT |
|---|---|---|
| 01/07 | 0800 | CHECK NIPRIDE INFUSION SITE |
| | 0800 | NEURO VITAL SIGNS |
| | 0800 | BAG & SUCTION USING STERILE TECHNIQUE |
| | 0800 | ASSESS LUNG SOUNDS |
| | 0900 | BED GROUNDED AND WHEELS LOCKED |
| | 0900 | CHECK NIPRIDE INFUSION SITE |
| | 0900 | COMPLETE BED BATH & SKIN CARE |
| | 0900 | VALIUM TABLET 2mg ORAL qd PRN RESTLESSNESS |
| | 1000 | CHECK NIPRIDE INFUSION SITE |
| | 1000 | FOLEY CATH CARE PER PROTOCOL |
| | 1000 | ET TUBE POSITION CHANGE |
| | 1200 | AMPICILLIN 500mg IVPB IN 100cc D5W q6H |
| | 1600 | MORPHINE SULFATE 1-5mg IV q4h PRN SEVERE PAIN |

| FREQUENCY | SCHED TIME | ACTUAL TIME | DOSE | ROUTE/SITE | COMMENTS | INITIAL |
|---|---|---|---|---|---|---|
| qd | 0900 | 0911 | 2mg | ORAL | | |

[NEXT PAGE]

| START STOP | MEDICATION DOSE ROUTE | | | | |
|---|---|---|---|---|---|
| 01/05 0900 | VALIUM TABLET 2mg ORAL | | | | |
| 01/08 0900 | PRN RESTLESSNES | | | | |

[HOLD DOSE] [ ] [ ] [ ] [ ] [OK]

FIG. 8C

METRO MEDICAL CENTER      JAN 07 0911

BLOOD GAS RESULTS READY

JACKSON, DONALD M.    9NBURN
ATTENDING: CHARLES RICE, M.D.    MR#: 88-19-46

SECTIONS: FLOWSHEET ORDERS NCP ASSESSMENT LABS R.T. [KARDEX]

FORMS: [TASK LIST] DIAGNOSTIC STUDIES MEDICATIONS GENERAL CARE PERTINENT INFORMATION

| DATE | TIME | ORDER TEXT |
|------|------|------------|
| 01/07 | 0800 | CHECK NIPRIDE INFUSION SITE |
|  | 0800 | NEURO VITAL SIGNS |
|  | 0800 | BAG & SUCTION USING STERILE TECHNIQUE |
|  | 0800 | ASSESS LUNG SOUNDS |
|  | 0900 | BED GROUNDED AND WHEELS LOCKED |
|  | 0900 | CHECK NIPRIDE INFUSION SITE |
|  | 0900 | COMPLETE BED BATH & SKIN CARE |
|  | 1000 | CHECK NIPRIDE INFUSION SITE |
|  | 1000 | FOLEY CATH CARE PER PROTOCOL |
|  | 1000 | ET TUBE POSITION CHANGE |
|  | 1200 | AMPICILLIN 500mg IVPB IN 100cc D5W q6H |
|  | 1600 | MORPHINE SULFATE 1-5mg IV q4h PRN SEVERE PAIN |
|  | 1800 | AMPICILLIN 500mg IVPB IN 100cc D5W q6H |
|  | 2000 | MORPHINE SULFATE 1-5mg IV q4h PRN SEVERE PAIN |

[NEXT PAGE →]

[SIGN]

FIG. 9

METRO MEDICAL CENTER     JAN 07 0912

BLOOD GAS RESULTS READY

JACKSON, DONALD M.    9NBURN
ATTENDING: CHARLES RICE, M.D.    MR#: 88-19-46

SECTIONS: ASSESSMENT   LABS   R.T.   KARDEX

FORMS: [MAR]   VITALS   I/O   VENTILATOR   LABS   [FLOWSHEET]   NCP   ORDERS

| START STOP | MEDICATION DOSE ROUTE FREQUENCY | SCHED TIME | ACTUAL TIME | DOSE | ROUTE/SITE | COMMENTS | INITIAL |
|---|---|---|---|---|---|---|---|
| ROUTINE: | | | | | | | |
| 01/05 1200<br>02/01 0600 | AMPICILLIN   RIGHT ARM<br>500 mg IN 100cc D5W IVPB q6h | 0600<br>1200<br>1800 | 0615 | 500mg | RIGHT ARM | | LN |
| 01/05 0600<br>01/07 1800 | MYLANTA II   NG   q4H | 0600<br>1000<br>1400<br>1800 | 0600 | 30cc | | | LN |
| DRIPS IV'S: | | | | | | | |
| 01/05 0600 | NIPRIDE IN 250cc D5W LEFT ARM<br>10cc/HR. | | 0600 | 25mg | LEFT ARM | | LN |
| PRN: | | | | | | | |
| 01/05 0900<br>01/08 1900 | MORPHINE SULFATE<br>1.5mg IV   q4H<br>PRN SEVERE PAIN | 0700<br>1100<br>1500<br>1900 | 0700 | 5mg | IV | FOR PAIN WITH RELIEF | LN |
| 01/05 0900<br>01/08 0900 | VALIUM TABLET 2mg ORAL   qd<br>PRN RESTLESSNESS | 0900 | 0911 | 2mg | ORAL | | LN |

SIGN

FIG. 10

METRO MEDICAL CENTER — JAN 07 0912

BLOOD GAS RESULTS READY — JACKSON, DONALD M. — 9NBURN
ATTENDING: CHARLES RICE, M.D. — MR#: 88-19-46

SECTIONS: [FLOWSHEET] ORDERS NCP ASSESSMENT LABS R.T. KARDEX

FORMS: MAR VITALS [I/O] VENTILATOR LABS

| | 01/07 0600 | 0700 | 0800 | 0900 | 1000 | 1100 | 1200 | 1300 | 1400 | 1500 |
|---|---|---|---|---|---|---|---|---|---|---|
| INTAKE 250cc D5W WITH 25mg. NIPRIDE 10cc/HR. LEFT ARM | 10 | 10 | 10 | 10 | | | | | | |
| AMPICILLIN 500 mg IN 100cc D5W IVPB q6h RIGHT ARM | | 100 | 356 | | | | | | | |
| TOTAL INTAKE 354 | 10 | 110 | 10 | 10 | | | | | | |
| OUTPUT URINE NG OUTPUT 349 | 75 / 35 | 65 | 15 | 20 | | | | | | |
| TOTAL OUTPUT 350 | 110 | 65 | 15 | 20 | | | | | | |
| NET I/O 351 | -100 | 45 | -5 | -10 | | | | | | |
| CUMULATIVE I/O 355 | -100 | -55 | -60 | -70 | | | | | | |

NEW TIME COLUMN    CLOSE CHART

MEDICAL INFORMATION SYSTEM WITH AUTOMATIC UPDATING OF TASK LIST IN RESPONSE TO ENTERING ORDERS AND CHARTING INTERVENTIONS ON ASSOCIATED FORMS

This application is a continuation of prior application Ser. No. 07/268,323, filed Nov. 17, 1988.

RELATED INVENTIONS

1. System Control Structure of a Hospital Information System and Method of Using Same, invented by John Brimm et al., U.S. Ser. No. 116,614, filed on Nov. 3, 1987, and assigned to the assignee of the present invention.

2. Method for Generating Patient-Specific Flowsheets by Adding/Deleting Parameters, invented by Ronald Norden-Paul et al., U.S. Ser. No. 116,611, filed on Nov. 3, 1987, and assigned to the assignee of the present invention, now U.S. Pat. No. 4,878,175.

3. Clinical Task List with Charting Through the Task List onto Underlying Form and Automatic Updating of Task List, invented by John Brimm et al., U.S. Ser. No. 268,821, filed on even date herewith, and assigned to the assignee of the present invention, now abandoned, and U.S. Ser. No. 07/572,317, filed Aug. 24, 1990, (continuation).

TECHNICAL FIELD

This invention relates generally to automated hospital information systems, and, in particular, to a hospital information system in which a time-oriented task list is automatically generated from data which has been entered from physicians' and nursing orders onto one or more forms, and in which tasks may be charted by a system user directly onto one of such forms with automatic updating of the task list and other associated form(s).

BACKGROUND OF THE INVENTION

The present invention concerns an automated clinical records management system. Such system has utility, for example, in a hospital-based patient record-keeping system. Patient record-keeping systems are used for maintaining a wide variety of types of medical records concerning clinic or hospital patients Hand-written patient record-keeping systems have evolved through many years of careful refinement and enhancement into systems which maintain a detailed manual record of medical information concerning each patient. To meet the needs of different hospital entities (such as doctors, nurses, pharmacy, accounting, laboratory, etc.) requiring access to such medical information, in a manual record-keeping system various medical information is logged into multiple types of records.

In a typical manual patient record-keeping system a patient chart, usually in the form of a notebook, is maintained at the nursing station for each patient. The notebook is divided into a plurality of individual tabbed sections, such as Physicians Orders, Kardex, Nursing Care Plan, Nursing Assessment, and Laboratory.

Each of the above sections is further subdivided into a number of forms. The forms are those which are appropriate to the individual patient and/or such patient's physician. For example, within the "Laboratory" section there may appear forms for Chemistry, Hematology, Blood Gas, and Microbiology.

In addition, a "Flowsheet" chart is usually kept at the patient's bedside. On the "Flowsheet" chart there typically appear individual areas for Medications Records, Vital Signs, Intake/Output, Laboratory Results, and other categories which are dependent upon the patient's affliction, such as Ventilator, which would be used if a patient were placed on a ventilator One problem with a manual patient record-keeping system is the necessity to enter the patient name and associated personal identifying information such as i.d. number, bed location, etc. separately on each patient record form associated with a given patient This is typically done using an embossed card, similar to a credit card, containing the patient's personal information. However, this process consumes a certain amount of time, and errors may be result if two patients' cards are inadvertently switched.

Another problem with manual patient record-keeping systems is that, to meet the diverse requirements of the different hospital entities for whose benefit such patient records are kept, identical information must be recorded on different forms. Again this involves additional time-consuming work and frequently causes errors to be interjected into the patient records. In addition, desired patient information may be inaccessible to a legitimate user because it is stored on a form with which such user is unfamiliar or on a form which is being accessed by another user at that time.

A further problem with manual patient record-keeping systems is that it is difficult to extract patient care information for auditing and review purposes. For example, the Joint Commission on Accreditation of Healthcare Organizations (JCAH) stipulates many diverse requirements for providing documentation, and fulfilling such requirements is often difficult. Therefore, it would be beneficial to have a patient record-keeping system which provided a direct relationship between a physician's order and the documentation corresponding to that order (e.g. whether the order was completed, or the reasons that it wasn't completed).

It has been estimated that nurses' salaries account for 30%-40% of a hospital's operating budget, and that they spend 25%-40% of their time performing clerical and communications tasks. Because of changes in government regulation, insurance reimbursement policies, and competition, hospitals are increasingly under pressure to reduce their operational costs. As a result, hospital occupancy and patient length of stay have decreased, and more hospital patients are acutely ill. However, staffing levels have been reduced to cut costs. In addition, there often exist shortages of qualified nurses. Thus, hospitals are providing care for sicker patients with fewer people, and there is a significant need for making those people more productive through hospital automation.

To maximize the productivity of hospital staff and to maximize overall patient care by making optimum use of patient data, various automated clinical record-keeping systems have been proposed and even implemented.

While automated record-keeping systems are known which organize many types of information, including information relating to customers, clients, and even medical/dental patients, no automated clinical records management system is known which provides the unmistakable benefits of an automated system and yet which very closely parallels the organization and appearance of the conventional, familiar manual hospital records charting system.

In known automated hospital record-keeping systems the user interface is typically "machine-oriented". In a "machine-oriented" system the system typically waits for the user to generate commands. The user often must proceed several layers deep through a confusing hierarchy of on-screen menus to the desired screen level. Once there, it is all too easy for the user to forget which screen level he is working in, how he got there, how to return to a more fundamental screen level, and how to move to a different screen level or to a related screen level.

In a "user-friendly" system, the system electronically emulates the existing hospital forms on the screen display and provides easily accessible commands within the context of the form to let the user manipulate and review the information on such forms.

It would be very desirable to provide the users of an automated hospital record-keeping system with the capability of generating a time-oriented task list of all tasks which must be performed for each patient. In present record-keeping systems, time-oriented tasks are maintained on a variety of different forms or merely committed to memory, the result being that a nurse or other user must manually write up or attempt to remember a chronological checklist of tasks to be performed for each patient. Not only is the manual generation of such a list time-consuming, but all too frequently mistakes are made in recording such information or in recalling it from memory. Thus it has been found to be very desirable to generate a task list automatically from data which has been entered from physicians' and nursing orders.

In a manual clinical record-keeping system, when a nurse accomplishes a task, he/she must not only record its accomplishment on the associated form from which it originated, but he/she must also document on the manual checklist that the task was performed. Thus, it would be desirable if the tasks on such task list could be charted by a system user while viewing the task list and if the associated form(s) were automatically updated at the same time that each task on the task list is completed by the user. Additionally, it would be desirable to be able to chart directly from this chronological task list that a particular intervention or procedure has been performed without leaving the context of the chronological task list.

In addition, it would be desirable if a task could be charted by a system user directly onto one of the system forms and if, in so doing, the task list and any other associated form(s) were automatically updated.

It would also be desirable to automatically record the completion of each task and intervention as it is performed to complete the documentation requirement for proper patient care.

BRIEF SUMMARY OF THE INVENTION

In the automated clinical records management system of the present invention, there are at least two methods by which a system user can chart the completion of tasks. According to a first method (described and claimed in Related Invention No. 3 identified above), the system user may chart the completion of a task without leaving the context of the task list by opening a window into the appropriate underlying form and charting the task directly onto such form. When the system user signs the completion of the task, the task list and any associated form(s) are automatically updated at the same time as the task completion is recorded on the underlying form.

According to a second method, described and claimed herein, the system user may chart the completion of a task directly onto an appropriate system form, and when the system user signs the completion of the task on such form, the task list and any associated form(s) are automatically updated at the same time as the task completion is recorded on such system form.

Accordingly, it is an object of the present invention to provide an automated clinical records management system whose format closely resembles that of a manual clinical records management system, which automatically generates a time-oriented task list of tasks which must be performed for a patient in response to the entry of orders into appropriate system forms, and in which an item may be charted directly onto an appropriate system form with automatic updating of the task list and other associated form(s) upon signing by the system user.

These and other objects are achieved in accordance with a preferred embodiment of the invention by providing in a medical information system comprising a processing unit, a memory unit, and at least one terminal unit wherein the terminal unit comprises display means for displaying patient information to a terminal user and input means for the terminal user to enter patient information into the system and to provide commands to the system, a method of generating and implementing an integrated plan of care for a patient, the method comprising (a) displaying a first form on the display means, (b) using the input means, entering onto the first form an order concerning a medically-related task to be performed regarding the patient, the order being entered by a person responsible for providing medical care to the patient, (c) as a result of the order, automatically adding information to a second form, the second form comprising a list of related tasks to be performed regarding the patient and containing areas for recording by the person the corresponding times when the tasks are actually performed, (d) automatically generating a list of all tasks to be performed regarding the patient, including such task, (e) displaying at least a portion of the second form, including the information, (f) using the input means, entering onto the second form an indication that such task has been performed, and (g) automatically modifying the list of all tasks to reflect that such task has been performed.

BRIEF DESCRIPTION OF THE DRAWINGS

The invention is pointed out with particularity in the appended claims. However, other features of the invention will become more apparent and the invention will be best understood by referring to the following detailed description in conjunction with the accompanying drawings in which:

FIG. 4 shows a CENSUS information screen.

FIG. 5 shows an ORDERS SHEET Form in the ORDERS Section.

FIG. 6 shows a MEDICATION ADMINISTRATION RECORD Form in the FLOWSHEET Section.

FIG. 7 shows a TASK LIST Form in the KARDEX Section.

FIGS. 8A-8C show information screens illustrating how items can be charted directly from the Task List without leaving the context of the Task List.

FIG. 9 shows an updated MEDICATION ADMINISTRATION RECORD Form in the FLOWSHEET Section.

FIG. 10 shows an INTAKE/OUTPUT Form in the FLOWSHEET Section.

DETAILED DESCRIPTION

Overview of Patient Care

Figure 1:
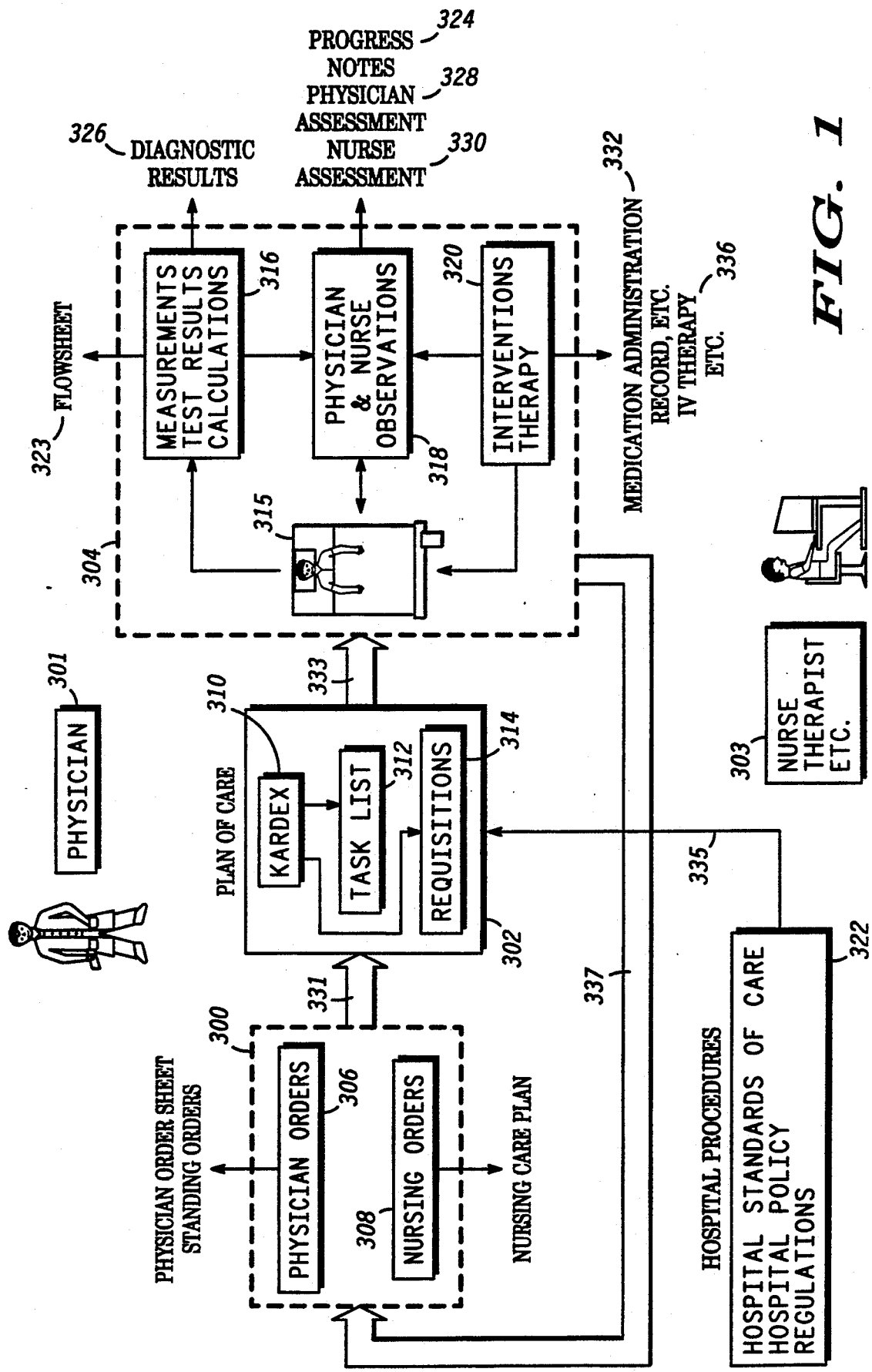
FIG. 1 shows a block diagram illustrating in general the patient care process in a typical hospital environment.

FIG. 1 shows a block diagram illustrating in general the patient care process in a typical hospital environment.

Physician 301 is responsible for the management and care of the patient 315 throughout the hospital stay. On admitting a patient to the hospital a physician will assess the patient and arrive at a diagnosis. Based on the diagnosis the physician will write a plan of care in his progress notes and generate a list of physician orders 306 to be executed by nursing and other hospital personnel 303. The physician's orders 306 are the source for the Kardex 310, Task List 312, Requisitions 314, and other associated forms that assist in the overall execution of the patient care plan 302. Nursing orders 308 also generate corresponding interventions in the Kardex 310 and Task List 312.

Other interventions in the Kardex 310 and Task List 312 are mandated by hospital procedures 322, which include hospital standards of care, hospital policy, and regulations. The nurse or other hospital personnel 303 executes the orders as written in the Kardex 310 and Task List 312 and then charts on the appropriate forms to satisfy the requirement for providing necessary documentation.

Other forms such as Flowsheet 323 and Diagnostic Results 326 document specific measurements, tests results, and/or calculations 316 performed directly on the patient or on the patient's tissue, fluids, etc. Similarly, interventions and other therapy 320 are documented on a Medication Administration Record form 332 and other forms.

The nurse and physician observe the patient 315 and the results of interventions and therapy 320 and document their observations 318 in progress notes 324 and other associated forms.

From the observations 318 and progress notes 324 the physician 301 or nurse 303 writes a new set of orders 300 corresponding to the present condition of the patient 315.

SYSTEM HARDWARE

Figure 2:
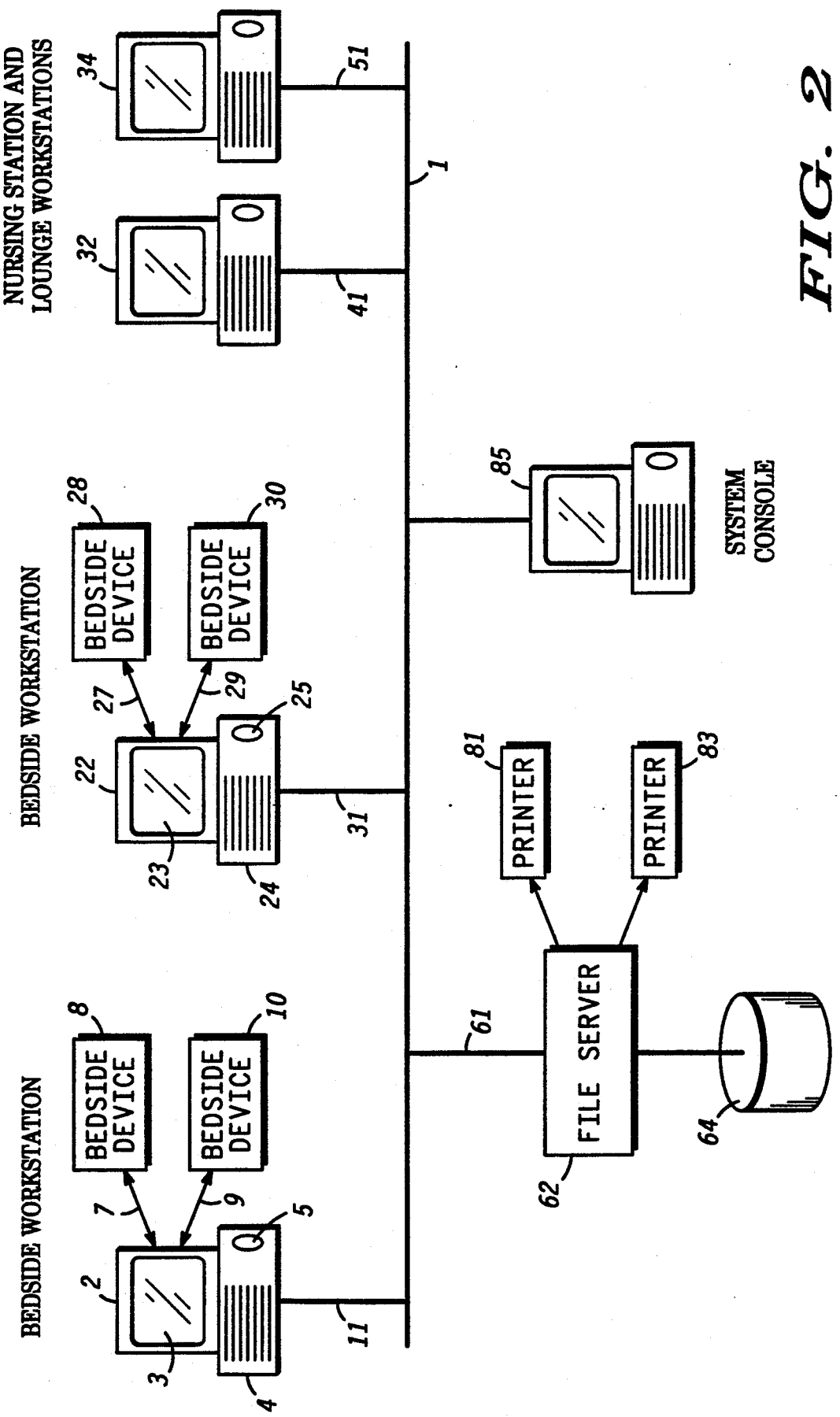
FIG. 2 shows a block diagram illustrating a preferred embodiment of a data processing system incorporating the automated clinical records system of the present invention.

Referring now to FIG. 2, a block diagram is shown of a typical hardware configuration for implementing the automated clinical records system of the present invention. FIG. 2 shows a distributed computer system comprising a plurality of workstations or terminals 2, 22, 32, 34, and 85 coupled to a local area network (LAN) 1.

The system is typically installed for use in a nursing care unit, such as an intensive care unit, in a hospital or clinic. Each of terminals 2 and 22 is located at the patient bedside. One terminal may be dedicated to the use of a single patient, or it may be used for multiple patients. Terminals 32 and 34 may be located at a nursing station or nurse/physician lounge area. Terminal 85 is the system console which is used by a system administrator to configure and maintain the system and to provide additional services, such as displaying system status and error messages, archiving, and performing diagnostics.

Each bedside workstation or terminal, such as terminal 2, includes a video display unit with a viewable screen 3 for displaying information to the viewer; a housing 4 containing computing, data storage, and communications equipment and having associated with it a keyboard and pointing device such as a mouse 5; and connections 7 and 9 to one or more bedside devices 8 and 10. Bedside devices 8 and 10 may take the form of patient monitoring equipment suitable for the patient undergoing care, such as an EKG monitor, respiratory monitor, etc. Bedside terminal 22 may be coupled to a different set of bedside devices 28 and 30 from those coupled to terminal 2.

The nursing station or lounge terminals 32 and 34, and system console 85, may be identical to those used in the patient care unit but without the bedside device connections, or they may comprise slightly different equipment (e.g. personal computers) so long as they provide similar functionality.

Also coupled to the LAN 1 is a file server 62 and associated disc storage device 64. The file server 62 provides controlled access by the workstations 2, 22, 32, 34, and 85 to write information to and read information from disc storage device 64.

Optionally coupled to LAN 1 may be interfaces (not shown) to couple various system peripheral equipment to the LAN 1. For example, remote access modems may be coupled to one of such interfaces to provide access to the system from remote terminals (not shown) located elsewhere in the hospital or located offsite, such as at a physician's residence. Remote access may also be employed to diagnose system problems from an off-site facility. A laboratory system may be connected to an interface to permit the communication of laboratory information between the laboratory system and the clinical management system. An order communication system may be coupled to an interface to permit orders to be communicated from the system to other hospital systems (e.g. pharmacy or laboratory) and vice versa. An archival storage device may be coupled to an interface to permit any information stored in the system to be safe-stored on suitable archival media, such as magnetic tapes or optical discs Printers 81 and 83 are coupled to file server 62 to allow patient information to be printed for the convenience of hospital personnel and to maintain a suitable legal record of all observations, orders, parameter readings, care plans, and other patient information regarding the monitored patients. Printers 81 and 83 may be any suitable printers such as, for example, laser printers or high speed dot matrix printers. A printer may optionally be coupled to the bedside terminal and/or the terminal at the nursing station or lounge, if desired.

In operation, the system user, typically a nurse or physician, conducts a dialog with the system through the use of the keyboard, mouse, or other appropriate means for entering information such as a light-pen, touch-pad, trackball, etc. "Icons", screen-sensitive areas, or the equivalent, or any combination thereof which is appropriate to the end application, may also be provided. "Icons" are symbols displayed on the screen whose functions are defined for the user by the system in view of the current screen context, and which can thus be readily changed according to the immediate requirements of the user application. In the present invention icons are selected by the system user by moving a screen cursor with the mouse and "clicking" on the icon, i.e., depressing the mouse button while the cursor overlies the icon.

The user provides information or queries to the system by means of the keyboard and/or pointing device(s), and he receives information from the system by means of information displayed on the screen and/or through audible signals which could include, in an alternative embodiment, speech synthesis.

Figure 3:
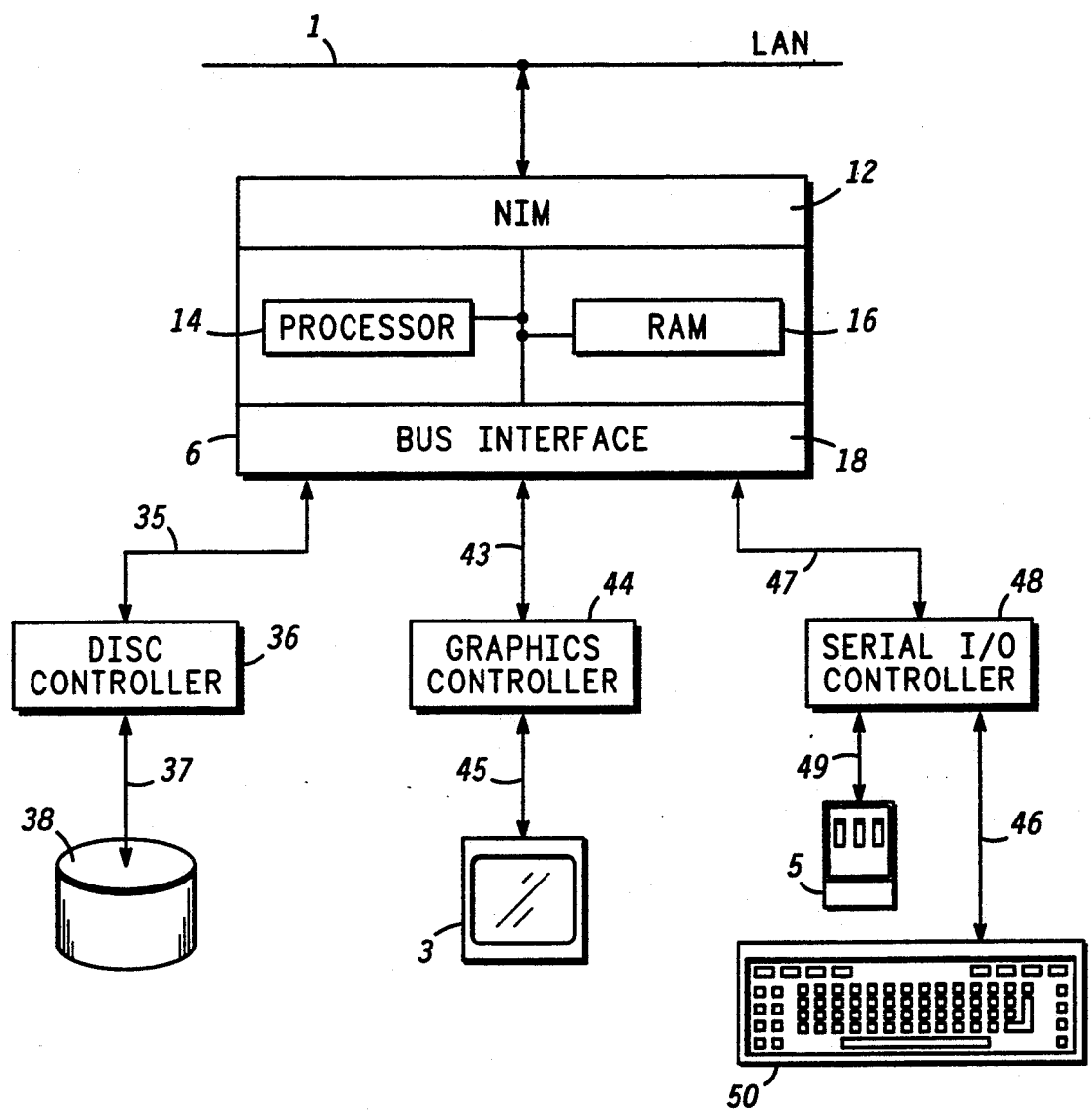
FIG. 3 shows a block diagram illustrating a processing unit associated with a workstation or terminal of the present invention.

FIG. 3 shows a block diagram illustrating a processing unit associated with a workstation or terminal of the present invention. Each terminal includes processing, storage, and communications functionality.

In FIG. 3 the Network Interface Module (NIM) 12 interfaces the terminal to the LAN 1. The terminal also comprises a processor 14, random access memory (RAM) 16, and a bus interface circuit 18. In a preferred embodiment of the invention the processor 14 is an MC68030 available from Motorola, Inc. A disc controller 36 is coupled to bus interface 18 via bus 35, and it is coupled to disc drive 38 via bus 37. A graphics controller 44 is coupled to bus interface 18 via bus 43 and to a video display unit (VDU) 3 via bus 45. A serial input/output controller 48 is coupled to bus interface 18 via bus 47, and it is coupled to mouse 5 via bus 49 and to keyboard 50 via bus 46.

CENSUS SCREEN

FIG. 4 shows a CENSUS information screen, which may be presented to the system user upon log-on or which may be accessed by the user from other levels in the system hierarchy. As shown, the CENSUS information screen comprises an area 70 which lists various wards in the hospital or clinic, such as 2NTU, 9NBURN, MICU, 9NICU, and CCU.

In the example shown, ward 9NBURN has been selected, and accordingly screen area 72 displays a list of rooms or beds 201-208. Screen area 74 displays the corresponding patients. Screen area 76 shows the corresponding patient I.D. numbers. Screen area 78 may be used for recording additional information pertaining to any patient.

The user may select a patient by pointing and clicking on the patient's name or I.D. number (if appearing in the screen) or on a room/bed number (if such room/bed is indicated as being unoccupied). The latter selection is made in order to admit a new patient.

After a patient has been selected by the user, the user is presented with several "softkey" options in the lower portion 80 of the screen shown in FIG. 4. The "softkey" options include TRANSFER, DISCHARGE, and OPEN CHART, identified by areas 84, 86, and 88, respectively. The user may then select a desired softkey option by depressing an associated key on the keyboard or by pointing and clicking with the mouse.

In addition to the TRANSFER, DISCHARGE, and other options, the user may select a patient (e.g. Donald M. Jackson) and then select the OPEN CHART softkey. This results in display of the default Section and default Form associated with the selected patient, for example as shown in FIG. 6 described below, wherein the FLOWSHEET Section and MEDICATION ADMINISTRATION RECORD Form are shown displayed to the user corresponding to this particular patient. The first Section and the first Form appearing in the list are shown by default. From that point the user can select other Sections and Forms for viewing as desired.

SECTIONS/FORMS HIERARCHY

As discussed in Related Invention #1 mentioned above, the automated clinical records management system of the present invention utilizes a two-level Sections and Forms organization or hierarchy, which closely resembles a manual patient charting system. This may be referred to as a "chart metaphor". Once a patient is selected from the CENSUS screen, all records pertaining to that patient are organized in a simple-to-comprehend two-level hierarchy, just as they would be if a manual record-keeping system were used.

Sections may be provided for all of the fundamental categories of patient records, such as physicians' chronological orders and active orders; organization of the orders into the Kardex and Task List; nursing assessments; nursing care plans; documentation of therapy including fluids, medication, etc.; recording of observations including monitored variables as well as laboratory results; and organization of all patient data into flowsheets, graphs, and notes. Since the objective is to provide comprehensive computer-based bedside decision support for the clinical staff in caring for patients, the number and type of Sections and Forms will necessarily vary by hospital as well as within the hospital. Sections and Forms will also vary by patient, individual physician, and workstation location.

For example, referring to FIG. 5, portion 152 of the screen contains a list of various Sections, including FLOWSHEET, ORDERS, NURSING CARE PLAN (NCP), ASSESSMENT, LABS, RESPIRATORY THERAPY (R.T.), and KARDEX. In this example the ORDERS Section has been selected, which is indicated to the user by the word "ORDERS" 203 appearing in inverse video. The two Forms appearing under the ORDERS Section are the ORDER SHEET and ORDER HISTORY, as shown in portion 154 of the screen. The ORDER SHEET Form has been selected by the user, and this is indicated by the words "ORDER SHEET" 209 appearing in inverse video on the screen.

In configuring the system for a particular institution, the system configurer, in cooperation with the institution, customizes a Task List for each hospital unit. Within the cardiology unit of a given hospital, for example, the Task List will normally appear in a certain standard format, whereas the Task List may appear in a slightly different format and with different content in the pediatrics unit.

An important advantage of the present invention is that all portions of the system are linked so that information can be shared among Sections and Forms with a single data entry. For example, once the patient demographics have been entered for a given patient, they appear identically on every form for that patient. Any amendment of the demographics for a given patient need be made only once, and it is automatically applied to every other form for that patient.

ENTRY OF ORDERS

FIG. 5 shows an ORDERS SHEET Form in the ORDERS Section.

The ORDERS SHEET Form is used to enter physician's orders for the selected patient. There are many types of physician orders, e.g. medication orders, lab orders, radiology orders, consultant orders (e.g. relating to care to be provided by other physicians) and orders relating to nutrition, psychiatric care, general health, etc.

The example to be discussed now with reference to FIG. 5 is a physician's order that a 2 mg. dosage of Valium be administered to a patient once a day, as needed, to reduce restlessness The Start Date is Jan. 5, 1988 and the Stop Date is Jan. 8, 1988.

After obtaining the appropriate entry into the system using predefined security measures the physician selects, from a list (not illustrated) the type of order he wants to enter (e.g. a medication).

The physician then selects from list 265 which medication (e.g. Valium) is to be prescribed by placing cursor 200 over the designation "Valium Tablet" and selecting with the pointing device. This immediately causes the words "Valium Tablet" to appear in the "Drug Name" screen area 269.

Next the physician fills in all other appropriate information in the corresponding spaces on the Medication Order Entry pop-up window 263, such as "Route", "Dose", "Frequency", "Number of Doses", "Start Date", and "Start Time", etc., either directly entering such information or selecting it from displayed lists. The system may default certain entry fields, such as "Route", "Dose", and "Frequency" to values conforming to hospital protocol for a given order.

Some information, such as "Order Date", "Order Time", and "Ordering M.D.", is already known by the system, and default values are automatically shown on the screen display. The physician may also enter a comment in the "Comments" space. After the order is electronically signed by the physician, it becomes active for that patient.

Once an order becomes active, information based on the order is automatically disseminated to all appropriate forms within the system.

For example, the same information appearing on the ORDER SHEET Form of the ORDERS Section is transferred on signing by the physician to the ORDER HISTORY Form, which is a chronological listing of all orders beginning with the patient's admission date. Additionally, a medication order entry would also be copied to the MEDICAL ADMINISTRATION RECORD Form of the FLOWSHEET Section, to the MEDICAL ADMINISTRATION RECORD Form of the KARDEX Section, and to the TASK LIST Form of the KARDEX Section as an intervention to be performed.

Regarding the medication options displayed in screen area 265 of FIG. 5, had Nipride been selected by the physician, then the Nipride order would have appeared on the TASK LIST Form of the KARDEX Section, on the MEDICAL ADMINISTRATION RECORD Form of the FLOWSHEET Section, on the INTRAVENOUS MEDICATION Form of the FLOWSHEET Section (no screen example shown), and on the INTAKE/OUTPUT Form of the FLOWSHEET Section.

FIG. 6 shows a MEDICATION ADMINISTRATION RECORD Form in the FLOWSHEET Section. The MEDICAL ADMINISTRATION RECORD Form provides information relating to and documents the administration of medications. The MEDICAL ADMINISTRATION RECORD Form shows the medication orders for the selected patient in a flowsheet format. The MEDICAL ADMINISTRATION RECORD Form is used by the nurse to record medications given to the patient as ordered by the physician. Medications may be added to or deleted from this form as the result of physician's orders. If a medication is not administered as ordered, the nurse may indicate this, along with the corresponding reason.

As described below, a nurse may chart interventions directly onto the MEDICAL ADMINISTRATION RECORD Form itself or the nurse may chart onto the appropriate portion of the MEDICAL ADMINISTRATION RECORD Form through a pop-up window of the TASK LIST Form.

In the left-hand column of area 156 of FIG. 6 appear the "Start" and "Stop" dates, with the "Start" and "Stop" times, for the corresponding medication orders.

The medication orders themselves may be divided into Routine medication orders and PRN (i.e. as required) medication orders. In the case of PRN orders, the particular symptom to be treated may be listed (e.g. severe pain, restlessness, etc.).

All pertinent medication order information is provided including the medication name (and generic name, if available), "Dose", "Route/Site", and "Frequency".

In order to view information which is part of the selected form but "off-screen", the user may scroll either horizontally or vertically by selecting an appropriate scrolling icon (not shown).

Regarding the order for Valium Tablets, the medication order information is provided in screen areas 237 and 239 of FIG. 6. Screen area 237 indicates that the first administration of Valium is to occur on Jan. 5 at 09:00 and that the final administration of Valium is to occur on Jan. 8 at 09:00. Screen area 239 provides the drug name, dosage, route/site, frequency, and a comment for the administration of Valium to the selected patient.

Following the medication orders area are columns for "Scheduled Time", "Actual Time", "Dose", "Route/Site", "Comments", and "Initials". The "Scheduled Time" column indicates when the medication is scheduled to be administered. The nurse indicates the actual time when the medication was administered in the "Actual Time" column.

For example, regarding the administration of Valium, screen area 271 indicates that the next scheduled administration of Valium is to occur at 09:00. The screen example shown in FIG. 6 represents information current as of 09:12 on Jan. 7, as shown in the upper right-hand corner of the screen. In screen area 272 the actual time when Valium was administered is shown as 09:11. Screen area 273 shows the dose to have been 2 mg. Screen area 274 shows the route/site to have been "oral". In highlighted screen area 238 the nurse's initials are indicated by default as "LN", representing the nurse who administered the Valium medication. By signing with the "Sign" softkey 277, the nurse may validate the default initials shown in screen area 238.

The MEDICAL ADMINISTRATION RECORD Form shown in FIG. 6 may document the administration of medications for one shift, a 24-hour period, or some other hospital-defined period.

Information may be logged onto the MEDICAL ADMINISTRATION RECORD Form in one of two ways: directly by appropriate entry of information onto the MEDICAL ADMINISTRATION RECORD Form, as described herein with reference to FIG. 6, or through a window into the TASK LIST Form, as described below with reference to FIGS. 8A-8C. If the nurse charts directly on the MEDICAL ADMINISTRATION RECORD Form, the corresponding forms are automatically updated, including the TASK LIST Form.

To enter an item of information directly onto the MEDICAL ADMINISTRATION RECORD Form, the nurse first selects the desired field for entry. The nurse may then change the defaulted actual time if the medication was administered at a different time other than the scheduled time and verify dose, route, and add any pertinent comments. On completion of entry, the nurse signs the record. On signing the record the proper initials of the nurse appear on the form.

This information is distributed to all corresponding forms, and the 09:00 entry on the Task List is automatically removed. The entry optionally may be shown on a corresponding form to the Task List that shows all tasks completed (e.g. TASK LIST HISTORY Form, not illustrated).

CREATION OF TASK LIST

Regarding the Task List itself, FIG. 7 shows an information screen representing the first page of a TASK LIST Form in the KARDEX Section.

The Task List is a time-oriented list of all actions or interventions that are to be performed during a given shift (or other defined period) as a result of physicians' orders and nursing orders.

The Task List is created automatically as a result of physicians' and nursing orders. The Task List automatically incorporates orders entered from the ORDERS SHEET Form in the ORDERS Section or from any of several forms of the NURSING CARE PLAN Section.

By capturing the content of the order at the source, the system of the present invention eliminates the need for the nurse or other hospital personnel to manually transcribe the relevant information from one form to another. In addition, all actions taken by the user in charting items from the Task List are documented on the appropriate forms for later retrieval.

With specific reference to FIG. 7, the Task List screen comprises an area 156 which lists in chronological sequence each action or intervention to be performed for the selected patient. For example, one of the actions to be taken at 09:00 is the administration of a 2 mg. Valium tablet, if needed, for restlessness.

CHARTING FROM THE TASK LIST

FIGS. 8A-8C show various information screens illustrating how a system user can chart from the Task List corresponding to a selected patient.

The user can chart directly without exiting the Task List by selecting an item on the Task List and recording an indication that some appropriate action has been taken with respect to it. A window is opened to the appropriate portion of the underlying form while simultaneously displaying the appropriate portion of the Task List. The action is then recorded on the underlying form and is also automatically copy-forwarded to all other appropriate forms (e.g. forms within the FLOWSHEET Section, NURSING CARE PLAN Section, etc.).

With specific reference now to FIG. 8A, the user has selected the 09:00 administration of Valium by moving the cursor arrow 200 adjacent the desired item and selecting with the pointing device 5 (refer to FIG. 2). Area 256 is then highlighted as shown in FIG. 8A, and the "CHART" softkey 258 appears in the lower part of the display.

Next the user selects the "CHART" softkey 258 to indicate that he or she is ready to chart. As shown in FIG. 8B, this opens a pop-up window 259 onto the MEDICAL ADMINISTRATION RECORD Form of the FLOWSHEET Section (shown in FIG. 6) relating to the charting of medications and specifically row 252 (FIG. 6) relating to the Valium order. The information displayed in pop-up window 259 (FIG. 8B) is identical to that which appears in row 252 of the MEDICAL ADMINISTRATION RECORD Form of the FLOWSHEET Section (FIG. 6).

The actual MEDICAL ADMINISTRATION RECORD Form will differ slightly from the pop-up window into the MEDICAL ADMINISTRATION RECORD Form which is entered via the TASK LIST Form, in that the former displays both charted and future charting times, whereas the latter displays only the current charting time.

Still referring to FIG. 8B, the nurse then charts directly onto the pop-up window 259 by selecting the area within pop-up window 259 which displays the appropriate intervention or procedure.

The nurse may then document the exact time the medication was given by moving cursor 200 to the "Actual Time" field 260 and depressing the select button on the pointing device 5. Field 260 becomes highlighted, and the nurse may change the defaulted time, if desired, by making an appropriate keyboard entry.

The nurse then may check the indicated dose and site, making changes if necessary, enter a comment if desired, and then validate the entries by selecting the "OK" softkey 278. This causes the pop-up window 259 to disappear. The information regarding the 09:00 Valium administration appears highlighted to reflect the charting action. When the nurse signs for all unsigned charting on the form by selecting the "Sign" softkey 279, the screen changes to what is shown in FIG. 8C. The screen shown in FIG. 8C reflects that the 09:00 Valium administration was made, since this intervention is no longer visible on this form.

As each item is charted (and signed) from the Task List, it is removed from the user's view. However, interventions or procedures that are not accomplished during that shift are maintained on the Task List for the next shift or for the next 24-hour period.

As each item on the Task List is charted, the corresponding item on the appropriate form(s) is also automatically charted This is seen from FIG. 9, which shows a MEDICATION ADMINISTRATION RECORD Form in the FLOWSHEET Section. Areas 272-275 have just been updated on this form by the Task List charting action described above.

The content of row entry 252 is identical to that shown in row 259 of the Task List example shown in FIG. 8B and shows the 2 mg. Valium administration, the scheduled time of 09:00, the actual time of 09:11, the dose, and the route.

Generally speaking, charting from the Task List may be performed on any intervention or procedure displayed on the TASK LIST Form. While the user is in effect charting directly onto the appropriate form through the pop-up window on the Task List, the user remains within the context of the TASK LIST Form. Charting within the Task List provides significant advantages since the user need not leave the Task List to chart on other forms within the system.

CHARTING DIRECTLY FROM THE FORM

In the example shown and described above, the user charted on the MEDICAL ADMINISTRATION RECORD Form of the FLOWSHEET Section through the TASK LIST Form. As indicated earlier, the user may also choose to chart directly on the appropriate form in the system such as the MEDICAL ADMINISTRATION RECORD Form.

Additionally, charting changes made to the MEDICAL ADMINISTRATION RECORD Form of the FLOWSHEET Section, either directly or through a window of the TASK LIST Form, are automatically displayed on all other appropriate forms within the system.

For example, assume that the nurse at time 07:00 had charted the infusion of a 500 mg. dose of Ampicillin given in a 100 cc. D5W solution to the patient beginning at the scheduled time of 06:00, and assume that the nurse had charted this directly onto the "Drips IV's" portion of the MEDICAL ADMINISTRATION RECORD Form of the FLOWSHEET Section. Then this charting action would have been automatically recorded as charted on the TASK LIST Form of the KARDEX Section, on the INTRAVENOUS MEDICATION Form of the FLOWSHEET Section (no screen example shown), and on the INTAKE/OUTPUT Form of the FLOWSHEET Section.

This is illustrated in FIG. 10 which shows an INTAKE/OUTPUT Form of the FLOWSHEET Section. The INTAKE/OUTPUT Form indicates hourly charting times across the top of the form, and it indicates "INTAKE", "TOTAL INTAKE", "OUTPUT", "TOTAL OUTPUT", "NET I/O", and "ACCUMULATIVE I/O" along the left-hand side of the chart.

Under the "INTAKE" heading, the Nipride and Ampicillin IV's are shown by rows 346 and 347, respectively. The Nipride infusion is a drip at the rate of 10 cc./hour. The 10 cc. amount infused during the previous hour is charted by the nurse at the conclusion of each hourly period. Thus the 10 cc. appearing under the 07:00 heading represents that which was administered since 06:00.

The Ampicillin order was for 500 mg. to be administered in 100 cc. of D5W (5% dextrose solution in water) every six hours, beginning at 06:00. This task would have appeared on the TASK LIST Form (FIG. 7) in the same format as is shown for the 12:00 and 18:00 administrations of Ampicillin.

Referring now to FIG. 6, let us assume the nurse started the Ampicillin administration at 6:00. When the Ampicillin I.V. administration was completed (assume at 06:15), the nurse would have charted the completion along with the completion time (06:15) and signed the Form. Then the 06:00 administration of Ampicillin would have been removed from the TASK LIST Form.

In addition, under the 07:00 time column on the INTAKE/OUTPUT Form (refer to FIG. 10), where all fluid intake and output during the previous hour is summarized, the 100 cc. of fluid intake occurring during the Ampicillin administration would have been recorded, as shown by reference numeral 356 in FIG. 10.

The TOTAL INTAKE in row 354 is the sum of the intake from the Nipride drip and any Ampicillin administration. At time 07:00 the TOTAL INTAKE is shown as 110 cc.

The OUTPUT (reference numeral 349) includes Urine and Nasal/Gastro (NG) headings, and at 07:00 the TOTAL OUTPUT (reference numeral 350) is shown to be 65 cc.

The NET I/O (reference numeral 351) is the difference between the TOTAL INTAKE and the TOTAL OUTPUT, which in this case is 45 cc. The CUMULATIVE I/O (reference numeral 355) indicates the change in INTAKE or OUTPUT throughout the day. Assuming that the CUMULATIVE I/O was −100 cc. at 06:00, if the NET I/O at 07:00 was 45 cc., then the CUMULATIVE I/O at 07:00 is (−100 cc.) plus 45 cc. which equals −55 cc.

Thus, in summary, the charting directly upon the MEDICAL ADMINISTRATION RECORD Form of the 06:00 administration of Ampicillin was automatically recorded both on the TASK LIST Form (by removal of this task) and on the INTAKE/OUTPUT Form (by recording the 100 cc. fluid intake).

DISCUSSION OF APPENDIX

The Appendix, Part I, provides a pseudo-code outline of the software for generating a Task List from the entry of at least one order. In the case illustrated, the order is the above-described physician's order for the administration of Valium.

Part II provides an outline of the software for charting from an underlying form, e.g. the MEDICAL ADMINISTRATION RECORD Form, and updating associated forms.

It will be apparent to those skilled in the art that the disclosed invention may be modified in numerous ways and may assume many embodiments other than the preferred form specifically set out and described above.

For example, the content, selection and number of Task Lists may be determined to meet the particular requirements of the system users. Also the particular hardware system on which the patient record-keeping system is implemented is a matter of choice. In addition, the number of workstations which may be coupled to the network is arbitrary and depends upon the user application.

Accordingly, it is intended by the appended claims to cover all modifications of the invention which fall within the true spirit and scope of the invention.

APPENDIX

PART I. GENERATION OF TASK LIST FROM ORDER ENTRY

1. Select patient.
    A. Display Patient Census screen.
        i. Display "Room/Bed", "Patient Name", "Patient I.D.", and "Admit Date".
        ii. Repeat 1.A.i. for each patient on list.
    B. Select Patient.
        i. Select patient by placing cursor over any portion of "Patient Name" field and pressing select button.
        ii. Highlight selected Patient Name.
        iii. Display "Transfer", "Discharge", and "Open Chart" softkeys.
2. Select "Open Chart" softkey.

A. Select "Open Chart" softkey by placing cursor over "Open Chart" softkey and pressing select button.
B. Open patient file by reading from selected Patient Database.
3. Display Sections & Forms for selected patient.
   A. Display Section: "ORDERS" and Form: "ORDER SHEET".
   B. Display Form: "ORDER SHEET" by displaying sort of "active orders".
   C. Display "New Order" softkey.
4. Select "New Order" softkey.
   A. Select "New Order" softkey by placing cursor over "New Order" softkey and pressing select button.
   B. Display pop-up window with entry field labeled "Select Order Entry Type".
   C. Display pop-up window with list of Order categories.
   D. Select Order category "MEDS".
   E. Display "Medication Order Entry" pop-up window.
      i. Display label "Medication Order Entry".
      ii. Display editable fields "Order Date", "Order Time", "Ordering M.D.", "Drug Name", "Route", "Dose", "Frequency", "Number of Doses", "Start Date", "Start Time", "Stop Date", "Stop Time", and "Comments".
      iii. Default "Order Date" to current date; "Order Time" to current time; "Ordering M.D." to initials of logged-on physician; "Start Date" to current date; and "Start Time" to current time.
      iv. Select "Drug Name" entry field by placing cursor over "Drug Name" entry field and pressing select button; highlight "Drug Name" entry field.
         a. Display additional pop-up window with Medication List.
         b. Select medication "Valium Tablet" by placing cursor over "Valium Tablet" field and pressing select button.
         c. Close Medication List pop-up window.
         d. Display "Valium Tablet" in "Drug Name" entry field in Medication Order Entry pop-up window.
      v. Default most common "Route", "Dose", and "Frequency" based on hospital or unit procedure.
      vi. Edit "Dose".
         a. Select "Dose" field by placing cursor over "Dose" field and pressing select button.
         b. Modify "Dose" entry with keyboard entry.
      vii. Repeat 4.E.vi. for other editable fields listed in 4.E.ii.
      viii. Select "Comment" field and enter appropriate comment.
      ix. Select "OK".
      x. Check for required fields and edits (e.g. "Number of Doses" field has valid entry; "Dose" appropriate with field edit requirements)
      xi. Close Medication Order Entry pop-up window.
      xii. Display Form: "ORDER SHEET" with update showing new order under "MEDS" heading.
5. Sign order.
   A. Select "Sign" softkey by placing cursor over "Sign" softkey and pressing select button.
   B. Check for data base consistency (e.g. duplicate order).
   C. Accept "Sign" of order.
6. Expand schedule (i.e. indicate medication administration times based on frequency and hospital policy).
   A. Based on hospital/unit policy expand schedule for shift and day.
7. Fan-out of information from order upon selecting "Sign" softkey.
   A. Copy-forward information to Section: FLOWSHEET, Form: MEDICAL ADMINISTRATION RECORD.
      i. Copy-forward "Drug Name" "Route/Site", "Dose", "Frequency", "Start/Stop Time", "Scheduled Time", "Actual Time", "Comments", and "Initial" to appropriate locations on screen.
   B. Copy-forward information to Section: KARDEX, Form: TASK LIST.
      i. For a given shift or day, copy-forward the medication administration times and insert chronologically within the schedule.
      ii. Copy-forward "Drug Name", "Dose", "Route/Site", "Frequency", and "Comment".
8. Chronological sort of tasks associated with order.
   A. Decompose order into set of time-based tasks.
   B. Sort all tasks by date.
   C. Sort all tasks for each date by time.

PART II. CHARTING FROM MEDICATION ADMINISTRATION RECORD FORM

1. Select Section: "FLOWSHEET".
   A. Place cursor over "Flowsheet" designation and press select button.
   B. Display Section: "FLOWSHEET", Form: "MEDICAL ADMINISTRATION RECORD".
2. Select medication to be charted by placing cursor over medication field and pressing select button.
   A. Select "Actual Time" by placing cursor over "Actual Time" field and pressing select button.
   B. Default "Actual Time" to "Scheduled Time", charted "Dose" to order "Dose", and charted "Route/Site" to order "Route/Site" and display.
   C. Optionally enter actual time of medication administration from keyboard.
   D. Edit charted "Dose", charted "Route", and/or "Comment" in similar fashion.
3. Verify by selecting "OK" softkey.
   A. Place cursor on "OK" softkey and press select button.
   B. Display and highlight initials of logged-on user.
4. Select "Sign" softkey.
   A. Place cursor over "Sign" softkey and press select button.
5. Fan-out of information to Task List and other appropriate forms on "Sign".
   A. Copy-forward the entered "Actual Time", charted "Dose", charted "Route/Site", and/or "Comment" to appropriate forms (e.g. Task List, INTAKE/OUTPUT Form of FLOWSHEET Section, etc.)

What is claimed is:

1. In a medical information system comprising a processing unit, a memory unit, and at least one terminal unit wherein said terminal unit comprises display means for displaying patient information to a terminal user and input means for said terminal user to enter patient information into said system and to provide commands to said system, a method of generating and implementing an integrated plan of care for a patient, said method comprising:

(a) displaying a first form on said display means;
(b) using said input means, entering onto said first form an order concerning a medically-related task in the form of an action or intervention to be performed regarding said patient, said order being entered by a person responsible for providing medical care to said patient, such as a physician or nurse;
(c) as a result of said order, automatically transcribing information relating to said task to a second form, said second form comprising a list of related tasks to be performed regarding said patient and containing areas for recording by a person responsible for performing said tasks corresponding indications that said tasks are actually performed;
(d) automatically and substantially instantaneously transcribing information relating to said task to a third form, said third form comprising a list of all tasks to be performed regarding said patient, including said related tasks of said second form, and further including all other actions and interventions ordered or to be ordered for said patient as a result of physician's orders or nursing orders;
(e) displaying at least a portion of said second form, including said information, to said person responsible for performing said tasks;
(f) using said input means, entering onto said second form an indication that said task has been performed; and
(g) automatically and substantially instantaneously modifying said third form to reflect that said task has been performed.

2. In a medical information system comprising a processing unit, a memory unit, and at least one terminal unit wherein said terminal unit comprises display means for displaying patient information to a terminal user and input means for said terminal user to enter patient information into said system and to provide commands to said system, a method of generating and implementing an integrated plan of care for a patient, said method comprising:

(a) displaying a first form on said display means;
(b) using said input means, entering onto said first form an order concerning a medically-related task in the form of an action or intervention to be formed regarding said patient, said order being entered by a person responsible for providing medical care to said patient, such as a physician or nurse;
(c) as a result of said order, automatically transcribing information relating to said task to a second form, said second form comprising a list of related tasks to be performed regarding said patient and containing areas for recording by a person responsible for performing said tasks corresponding indications that said task are actually performed;
(d) automatically and substantially instantaneously transcribing information relating to said task to a third form, said third form comprising a list of all tasks to be performed regarding said patient, including said related tasks of said second form, and further including all other actions and interventions ordered or to be ordered for said patient as a result of physicians' orders and nursing orders;
(e) displaying at least a portion of said second form, including said information, to said person responsible for performing said tasks;
(f) using said input means, entering onto said second form an indication that said task has been performed;
(g) automatically and substantially instantaneously modifying said third form to reflect that said task has been performed; and
(h) automatically adding information relating to the completion of said task to a fourth form, said fourth form comprising a list of information regarding said patient.

* * * * *